United States Patent [19]

de Kanawati et al.

[11] Patent Number: 5,010,898

[45] Date of Patent: Apr. 30, 1991

[54] HEAD SUPPORTING AND SUSTAINING APPARATUS

[75] Inventors: Gisleine C. de Kanawati; George G. Philot, both of Sao Paulo, Brazil

[73] Assignee: Mara Teixeira De Freitas, Sao Paulo, Brazil

[21] Appl. No.: 524,298

[22] Filed: May 15, 1990

[30] Foreign Application Priority Data

May 16, 1989 [BR] Brazil ................................. 8902279

[51] Int. Cl.⁵ ............................................. A61F 5/37
[52] U.S. Cl. ...................................... 128/845; 128/75; 128/78
[58] Field of Search ............... 128/848, 857, 163, 878, 128/75, 78, 97.1, 76 R

[56] References Cited

U.S. PATENT DOCUMENTS

| 4,539,979 | 9/1985 | Bremer | 128/75 |
| 4,632,099 | 12/1986 | Mollo | 128/78 |
| 4,732,144 | 3/1988 | Cunanan | 128/878 |
| 4,800,897 | 1/1989 | Nilsson | 128/782 |
| 4,869,240 | 9/1989 | Boren | 128/75 |

Primary Examiner—Robert A. Hafer
Assistant Examiner—Kerry Owens
Attorney, Agent, or Firm—Olson & Hierl

[57] ABSTRACT

An apparatus for supporting and sustaining the head of a paralyzed individual in an upright position allows the individual to move freely. The apparatus comprises a mounting assembly associated with a support element, a hanger member connected to the mounting assembly, an attachment for supporting the head of the patient and a resilient element connecting the head supporting attachment to the hanger member, whereby the head of the patient is movably supported in an upright position.

16 Claims, 2 Drawing Sheets

5,010,898

HEAD SUPPORTING AND SUSTAINING APPARATUS

FIELD OF THE INVENTION

The present invention generally relates to therapeutic devices for supporting body members of individuals with physical disabilities and, in particular, to an apparatus for supporting and sustaining the head of a paralyzed patient.

BACKGROUND OF THE INVENTION

It is widely known by those skilled in the art that patients who suffer from paralysis due to a dysfunction of the brain have little or no control over their body muscles. As a result, it is impossible for such patients to maintain proper posture. An upright posture is extremely important in any therapeutic treatment to reduce the problems derived from this condition.

Due to the complete lack of control which is inherent to this condition, the therapy for a recovering patient who suffers from paralysis is hampered from the onset by the improper posture acquired by the patient.

A previously proposed solution to this problem was the use of a chair provided with a plurality of safety belts, particularly designed to fasten the legs, arms and body of the patient in order to support and sustain the body in a more suitable position for the physiotherapeutic exercises used to help the patient improve control over his body.

The foregoing chair solved, at least partially, the problem of maintaining proper posture. However, the chair did not provide suitable support for the head, which drooped forward or sideways due to the patient's lack of control over the muscles in his neck.

Several research studies performed with a number of patients showed that this drooping of the patient's head produced an imbalance in the control center of the nervous system of the patient. This imbalance was extremely detrimental to the recovery of the patient since the imbalance and the drooping added significantly to the problem.

A second previously proposed solution to this particular problem was the use of a device for holding and supporting the patient's head to prevent it from drooping through the use of belts and straps to firmly fasten the head in an upright position.

Although this solution was a significant advancement when compared to the chair of the prior art, it was not good enough to allow the patient to satisfactorily accomplish the desired purposes.

In fact, the foregoing research studies showed, startlingly clearly, that the recovery of a patient improved considerably when the head of the patient was maintained in a movable upright position. This position is similar to the normal posture of those who do not suffer from this condition, wherein the head is maintained in an upright position from which it can move freely.

SUMMARY OF THE INVENTION

One object of the present invention is to solve the foregoing problems of the prior art by providing an apparatus for supporting and sustaining the head of a paralyzed patient in an upright position while allowing complete freedom of movement.

According to the present invention, this object is accomplished by the provision of an apparatus for movably supporting the head of a patient in an upright position comprising: means for mounting the apparatus on a support element, hanger means projecting from the mounting means, means for supporting and sustaining the patient's head, and resilient means connecting the head supporting and sustaining means to the hanger means, whereby the head of the patient is supported and sustained in an upright position from which it can freely move in response to a voluntary command from the patient.

BRIEF DESCRIPTION OF THE DRAWINGS

The present invention will be hereinafter described in greater detail with reference to a preferred embodiment shown in the attached drawings, which shall not be considered as limiting the invention wherein.

DESCRIPTION OF A PREFERRED EMBODIMENT

With reference to the drawings, a preferred embodiment of the head supporting and sustaining apparatus according to the present invention is shown for supporting the head of a paralyzed patient who suffers from a brain dysfunction. The apparatus comprises means for mounting the apparatus, hanger means projecting from the mounting means, means for supporting and sustaining the head of the patient, and resilient means connecting the supporting means to the hanger means.

Figure 1:
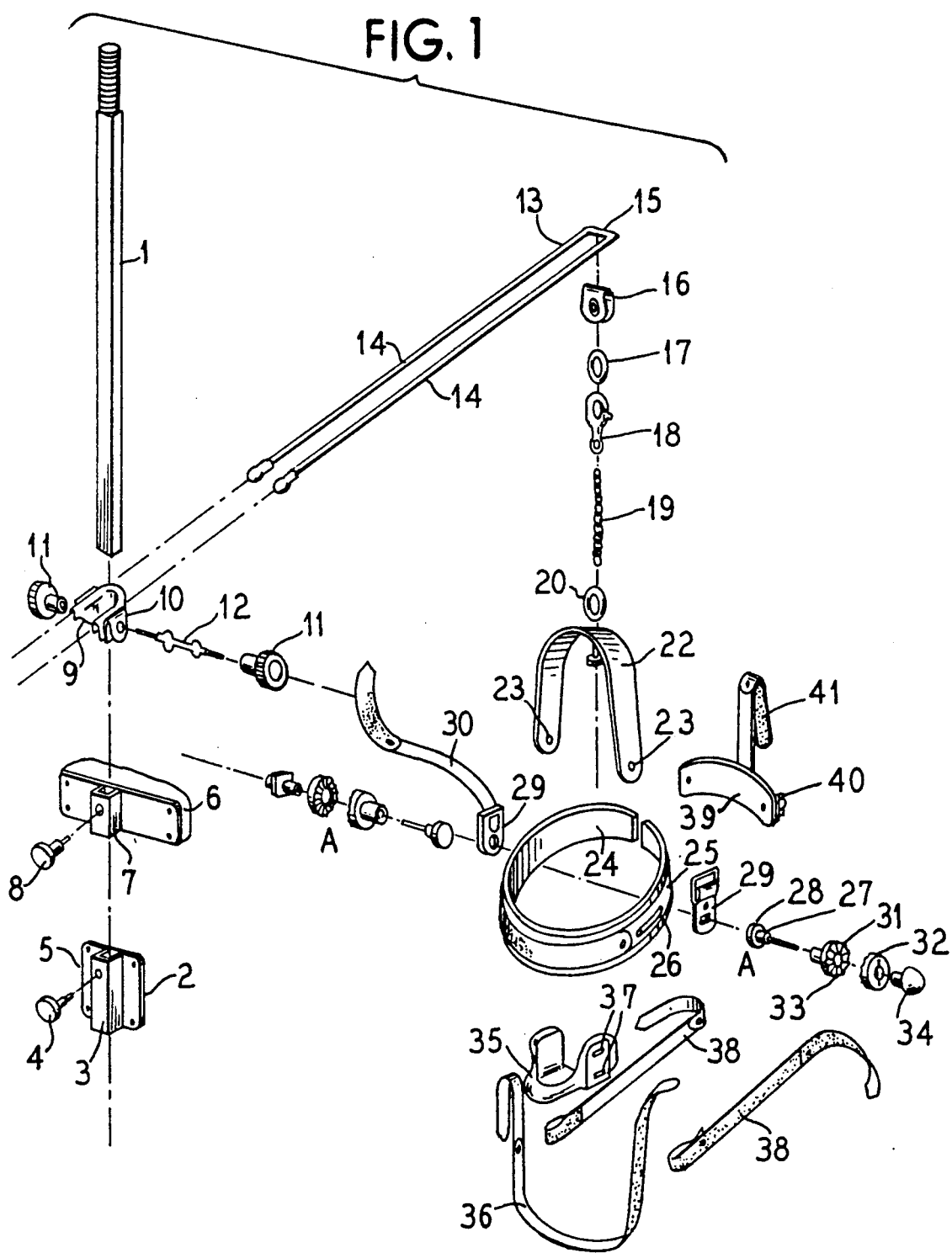
FIG. 1 is an exploded perspective view of the head supporting and sustaining apparatus according to the invention.
Figure 2:
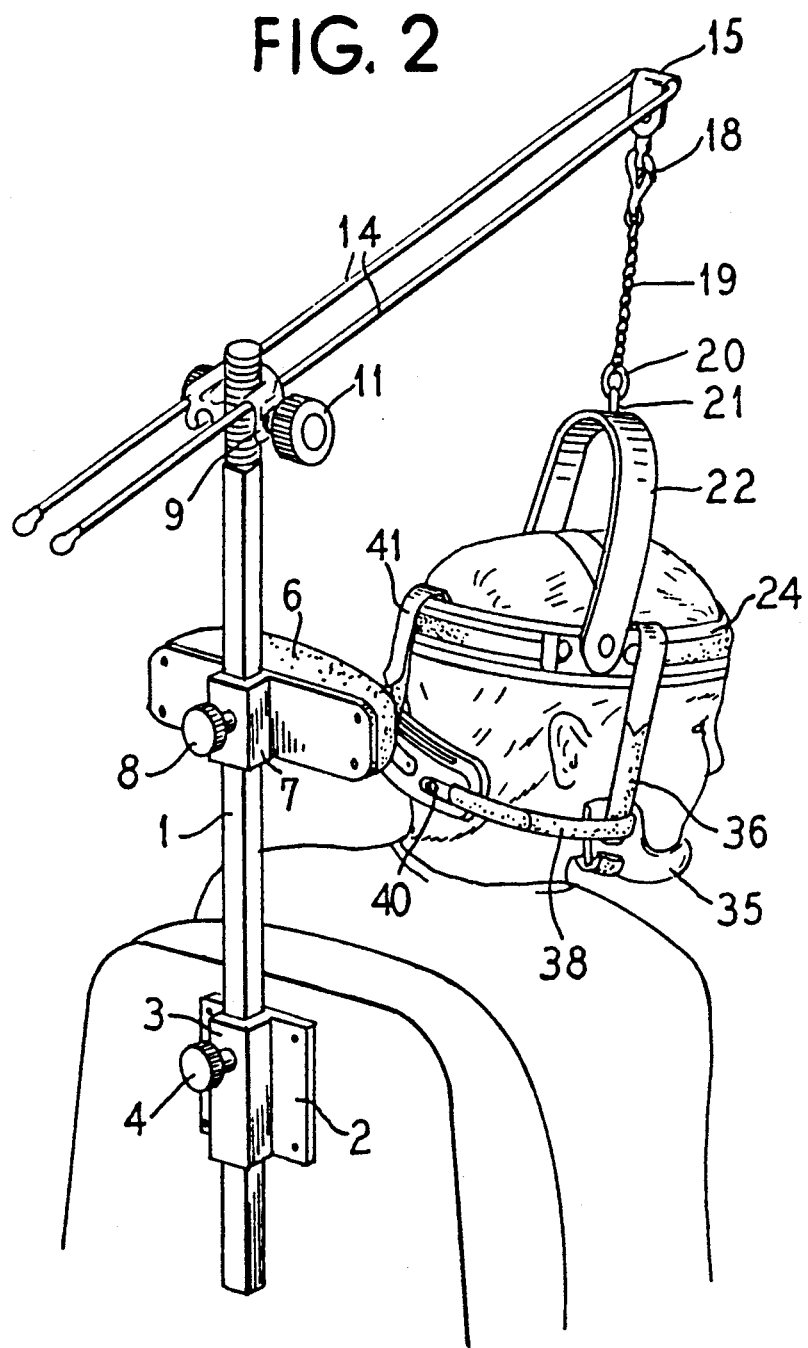
FIG. 2 is a perspective view of the head supporting and sustaining apparatus when used on a patient.

The mounting means is used for supporting the apparatus to a support element such as the back of a chair (see FIG. 2). The mounting means comprises a rod 1 having a substantially square cross-section that is slidably received in a guide member 3 formed in a mounting element 2 which is attached to the back of the support element by screws (not shown). A screw 4 in a threaded bore 5 drilled in the guide member 3 is used to position the rod 1 in a suitable position and thus prevent it from sliding.

A cushioned brace 6 is also supported by the rod 1 through a guide member 7, and a screw 8 similar to the screw 4 is used to position the brace in a suitable position along the rod 1. This cushioned brace 6 is used to provide a soft and comfortable support for the back of the patient's head in order to avoid injury due to a casual impact against the rod 1.

The hanger means is also attached to the rod 1 with a U-shaped bracket 9 which is used to adjust the length and the inclination of a projecting hanger member 13. The U-shaped bracket 9 is provided with lateral flanges 10 adapted to receive the legs 14 of the hanger member 13 therein. A threaded pin 12 which passes through the legs of the U-shaped bracket 9 cooperates with end threaded members 11 to firmly position the legs 14 in order to adjust the length and the inclination of the hanger member 13.

As mentioned above, the hanger member 13 is U-shaped, and comprises two parallel legs 14 joined by a central portion 15. A strap 16 surrounds the central portion 15 and a ring or link 17 is used to tie the ends of the strap 16.

A spring key 18 such as a snap or spring hook is releasably hooked to the ring or link 17. A helical spring 19 is connected at one of its ends to the snap hook 18 and, at its opposite end, to a second ring or link 20 attached to a strap 22 of the head supporting and sustaining means through a rivet 21 or the like.

The foregoing resilient means provides a stable support for the patient's head, while simultaneously allowing it to move freely.

The strap 22 of the head supporting and sustaining means, hereinafter referred to as a "helmet", is attached to a padded headpiece 24 through opposed openings 23 formed at its ends, which are received and held in position by affixing means which will be described in greater detail hereinafter.

The padded headpiece 24 is covered with an overbelt 25 formed with a slit 26 on each side and attached to the headpiece 24 by rivets (not shown).

A head portion 28 of a threaded fastening pin 27 is fixed between the headpiece 24 and the overbelt 25 so that the pin 27 projects perpendicularly from the headpiece 24 in order to receive and position the end members 29 of a crownbelt 30 which surrounds the head of the patient, a pair of matching disc elements 31 and 32 having radial grooves 33 on their matching inner surfaces, and a threaded end screw 34 which is used to hold the other members in position.

A chin supporting member 35 is also attached to the headpiece 24 through a belt 36 which passes through slits 37 formed on the chin supporting member 35. The belt 36 also receives a pair of additional belts 38 which attach the chin supporting member 35 to a padded support member 39 used to protect the back of the patient's head, where the additional belts 38 are received in connecting brackets 40. A third belt 41 is used to attach the padded back support member 40 to the headpiece 24.

The "helmet" as described above surrounds the head of the patient and provides a firm support thereto while, connected to the resilient means, allows the patient to freely move his head which is sustained in an upright position.

Having described the invention, it will be understood that the apparatus may include a number of modifications in various equivalent embodiments, as long as these modifications do not depart from the true spirit and scope of the invention as discussed herein and in the accompanying claims.

What is claimed is:

1. An apparatus for movably supporting the head of a patient in an upright position to a support element comprising:
   (a) means for mounting the apparatus on the support element comprising a slidable rod and a mounting element having a first guide member formed thereon for receiving the slidable rod, stop means for positioning the rod within the first guide member, and a second guide member comprising a cushioned brace and stop means thereon for slidably positioning the cushioned brace along the rod;
   (b) hanger means operatively associated with the mounting means;
   (c) means for movably supporting the head of the patient; and
   (d) resilient means connecting the supporting means to the hanger means whereby the head of the patient is supported and maintained in an upright position for relatively unrestrained movement by the patient.

2. The apparatus according to claim 1 wherein the hanger means comprises a U-shaped bracket and a U-shaped rod having a pair of parallel legs joined by a central portion, the parallel legs being received in the U-shaped bracket to adjust the length and the inclination of the hanger means.

3. The apparatus according to claim 2 wherein the U-shaped bracket comprises a pair of lateral flanges which receive and hold the legs of the hanger means.

4. The apparatus according to claim 1 wherein the means for supporting the head of the patient comprises a plurality of belts surrounding and firmly holding the head, the belts defining a helmet which protects the head of the patient.

5. The apparatus according to claim 1 wherein the resilient means comprises a helical spring connected to the head supporting means at one end and to the hanger means at an opposite end thereof.

6. The apparatus according to claim 5 including means for connecting the helical spring to the hanger means.

7. The apparatus according to claim 6 wherein the connecting means comprises a releasable hook.

8. An apparatus for movably supporting the head of a patient in an upright position comprising:
   (a) a support element including mounting means comprising a slidable rod and a mounting element having a first guide member associated therewith for receiving the slidable rod, stop means for positioning the rod relative to the first guide member, and a second guide member comprising a brace with stop means associated therewith for slidably positioning the brace along the rod;
   (b) hanger means operatively associated with the mounting means;
   (c) supporting means which can be removably secured about the head of the patient; and
   (d) resilient means connecting the supporting means to the hanger means whereby the head of the patient can be supported and maintained in an upright position for relatively unrestrained movement.

9. The apparatus according to claim 8 wherein the hanger means comprises bracket means and rod means having a pair of substantially parallel legs joined by a central portion, the legs being received in the bracket means whereby the length and the inclination of the hanger means relative to the mounting means can be adjusted.

10. The apparatus according to claim 9 wherein the bracket means comprises a pair of lateral flanges which receive and hold the legs of the hanger means.

11. The apparatus according to claim 9 wherein the bracket means is substantially U-shaped.

12. The apparatus according to claim 9 wherein the rod means is substantially U-shaped.

13. The apparatus according to claim 8 wherein the means for supporting the head of the patient comprises a plurality of belts surrounding and firmly holding the head, the belts defining a helmet which protects the head of the patient.

14. The apparatus according to claim 8 wherein the resilient means comprises spring means connected to the supporting means at one end and to the hanger means at an opposite end thereof.

15. The apparatus according to claim 14 including means for connecting the spring means to the hanger means.

16. The apparatus according to claim 15 wherein the connecting means comprises a releasable hook.

* * * * *